United States Patent
Oga et al.

(10) Patent No.: US 7,846,304 B2
(45) Date of Patent: *Dec. 7, 2010

(54) PROCESS FOR PURIFICATION OF 2-CHLORO-5-CHLOROMETHYL-1,3-THIAZOLE

(75) Inventors: Toshikazu Oga, Takasago (JP); Toru Kofukuda, Takasago (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/385,038

(22) Filed: Mar. 30, 2009

(65) Prior Publication Data

US 2009/0200154 A1    Aug. 13, 2009

Related U.S. Application Data

(62) Division of application No. 10/593,464, filed as application No. PCT/JP2005/004181 on Mar. 10, 2005, now Pat. No. 7,531,067.

(30) Foreign Application Priority Data

Mar. 22, 2004  (JP)  ............................. 2004-081810

(51) Int. Cl.
   *B01D 3/34*  (2006.01)
   *B01D 3/42*  (2006.01)
   *C07D 277/32* (2006.01)

(52) U.S. Cl. ............................. 203/2; 203/63; 203/66; 203/73; 203/80; 548/202

(58) Field of Classification Search ...... 203/2, 203/63, 66, 73, 80, 91; 548/202
See application file for complete search history.

(56) References Cited

U.S. PATENT DOCUMENTS

| 4,748,243 | A | 5/1988 | Beck et al. |
| 5,068,343 | A | 11/1991 | Beck et al. |
| 5,180,833 | A | 1/1993 | Uneme et al. |
| 6,214,998 | B1 | 4/2001 | Decker |
| 6,787,654 | B2 | 9/2004 | Krich et al. |
| 6,955,744 | B2 * | 10/2005 | Decker et al. ................. 203/63 |

FOREIGN PATENT DOCUMENTS

| EP | 0763531 | 3/1997 |
| EP | 0 794 180 | 9/1997 |
| EP | 1 219 613 | 7/2002 |
| GB | 1083910 | 9/1967 |
| JP | 63-83079 | 4/1988 |
| JP | 3-251575 | 11/1991 |
| JP | 4-234864 | 8/1992 |
| JP | 9-316062 | 12/1997 |
| JP | 2000-247963 | 9/2000 |
| JP | 2002-255948 | 9/2002 |
| WO | 02/12209 | 2/2002 |

OTHER PUBLICATIONS

Supplementary European Search Report issued Sep. 7, 2007 in the corresponding European Application.
Coulson et al., "Chemical Engineering", vol. 2, Third Edition, p. 478, 1959.

* cited by examiner

*Primary Examiner*—Virginia Manoharan
(74) *Attorney, Agent, or Firm*—Wenderoth, Lind & Ponack, L.L.P.

(57) ABSTRACT

The present invention provides a process for purifying 2-chloro-5-chloromethyl-1,3-thiazole represented by the formula (I):

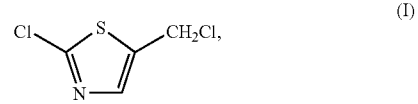

characterized in that a crude 2-chloro-5-chloromethyl-1,3-thiazole represented by the formula (I) is treated with a lower alcohol before the distillation, and then is distilled. The present purification process is a new one for purifying 2-chloro-5-chloromethyl-1,3-thiazole, suitable for industrial practice.

12 Claims, No Drawings

PROCESS FOR PURIFICATION OF 2-CHLORO-5-CHLOROMETHYL-1,3-THIAZOLE

This is a divisional of Ser. No. 10/593,464, filed Oct. 25, 2006, now issued as U.S. Pat. No. 7,531,067 on May 12, 2009, which is a U.S. national stage of International Application No. PCT/JP2005/004181 filed Mar. 10, 2005.

TECHNICAL FIELD

The present invention relates to a new process for purifying 2-chloro-5-chloromethyl-1,3-thiazole.

BACKGROUND ART

2-Chloro-5-chloromethyl-1,3-thiazole (hereinafter, abbreviated as CCT in some cases) is an important compound as an intermediate for producing biologically active compounds such as pesticides (see Patent Literature 1: JP-A No. 3-157308). As a typical method for preparing CCT, there has been a known method of reacting 2-chloroallyl isothiocyanate with a chlorinating agent (see Patent Literature 2: JP-A No. 4-234864). For purifying crude CCT prepared by the said method, the following methods have previously been known.

The above Patent Literature 2 has described a method of simply distilling under reduced pressure without performing a pretreatment for decomposing impurities present. The method requires attentions in terms of equipment and time, based on the necessity of setting a reflux ratio to obtain CCT in high purity, because the impurities are azeotropic with CCT. In other words, there is a problem of difficulty to suppress the content of azeotropic impurities present, when the distillation is performed under the whole distilling conditions without a reflux ratio. There is an additional problem that the azeotropic impurities have relatively high melting point and thus are condensed within a distillation equipment system, and the condensed impurities fixed in the equipment piping promote corrosion on the equipment, when the distillation is performed under the whole distilling conditions without a reflux ratio. Whereas, a problem arises that even when setting a reflux ratio to suppress contamination of the impurities, the period of distillation is prolonged, and distillation recovery of CCT is decreased due to low thermal stability of CCT. This tendency is naturally stronger with more increased charge per batch.

To solve the problems of the above purification method, Patent Literature 3 (JP-A No. 9-316062) has proposed a method of recrystallizing crude CCT using an organic solvent. This method, however, requires a large amount of solvent for crystallization, resulting in an expensive material cost. Further, the method requires equipments such as filters for crystal separation and filtration processing, resulting in an expensive cost of equipments. Moreover, since the resultant crystal has a melting point of 30° C., the method requires an equipment for controlling a filtration temperature during the separation of the crystal after the crystallization, resulting in a further cost of equipments and complicated processing operation. In addition, since the resultant crystal has harmful properties such as bad odor, and eye or skin irritation, it is undesirable to use a filter requiring a periodical maintenance such as replacing work of a filter fabric. Therefore, it is hard to say that the purification method by recrystallization is a really excellent one for industrial purification.

Under such a situation as described above, there is a need for a method of purifying CCT, which is less expensive, has good operability, and can recover CCT in high purity and high recovery.

DISCLOSURE OF THE INVENTION

Problems to be Solved by the Invention

The object of the present invention is to provide a new process for purifying CCT, suitable for industrial practice.

MEANS FOR SOLVING THE PROBLEM

As a result of the extensive investigation to solve the problems mentioned above, the present inventors have found that, upon purification of 2-chloro-5-chloromethyl-1,3-thiazole by distillation of a crude product thereof, by treating the crude product with a lower alcohol before the distillation, purified CCT can be obtained in high purity and high recovery without a specific reflux ratio and an extra distillation equipment during the distillation, and have accomplished the present invention.

That is, the present invention is:

(1) a process for purifying 2-chloro-5-chloromethyl-1,3-thiazole represented by the formula (I):

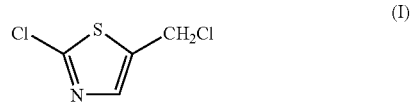

by distillation of a crude product thereof, comprising treating the crude product with a lower alcohol before the distillation;

(2) the process for purifying 2-chloro-5-chloromethyl-1,3-thiazole according to the above (1), wherein the treatment with the lower alcohol is carried out by adding the lower alcohol to the crude product of 2-chloro-5-chloromethyl-1,3-thiazole, followed by stirring;

(3) the process for purifying 2-chloro-5-chloromethyl-1,3-thiazole according to the above (1) or (2), wherein the crude product of 2-chloro-5-chloromethyl-1,3-thiazole is a reaction mixture or a residue obtained by distilling the solvent from the reaction mixture, wherein the reaction mixture is obtained by reacting a 2-halogenoallyl isothiocyanate represented by the general formula (II):

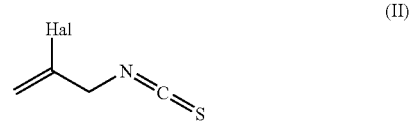

(wherein Hal represents a chlorine atom or a bromine atom) with a chlorinating agent in the presence of a solvent;

(4) the process for purifying 2-chloro-5-chloromethyl-1,3-thiazole according to the above (3), wherein the crude product of 2-chloro-5-chloromethyl-1,3-thiazole is a residue obtained by distilling the solvent from the reaction mixture;

(5) the process for purifying 2-chloro-5-chloromethyl-1,3-thiazole according to any one of the above (1) to (4), wherein the lower alcohol is methanol; and (6) the process for purifying 2-chloro-5-chloromethyl-1,3-thiazole according to any one of the above (3) to (5), wherein Hal is a chlorine atom.

EFFECTS OF THE INVENTION

According to the purification process of the present invention, crude CCT can be purified with a simple equipment under good operable conditions in a short time, and CCT can be obtained in high purity and high yield.

More specifically, since the purification process of the present invention surprisingly can convert impurities present in CCT into a compound not being azeotropic on distillation, the distillation can be performed without a reflux ratio, which has previously been set, in order to separate the impurities. Further, since no azeotropic impurities become present in CCT, the content of impurities in CCT after the distillation is markedly decreased. That is, highly pure CCT can be obtained in good distillation recovery.

Therefore, the purification process of the present invention can be performed without requiring the reflux ratio to be set in order to separate azeotropic impurities, and thus can reduce a cost of equipments for reflux piping such as rectifying columns and condensers. In addition, since the process can be performed without requiring the reflux ratio to be set, highly purified CCT can be obtained in a shorter time. The problem that impurities azeotropic with CCT are condensed within a distillation equipment system, and the condensed impurities fixed in the equipment piping system promote corrosion on the equipment, when the distillation is conducted under the whole distilling conditions without setting the reflux ratio in the purification process by simply distilling under reduced pressure without performing a pretreatment for decomposing impurities present is solved. Further, the purification process of the present invention has advantages capable of being practiced process using a large amount of solvent in a recrystallization process and without requiring an equipment for solid-liquid separation such as a filter. The purification process of the present invention is of course an advantageous purification process compared to the conventional method in a small scale, but dramatically exerts a more effect with a larger amount of charge.

BEST MODE FOR CARRYING OUT THE INVENTION

The crude product of CCT, to which the purification process of the present invention can be applied, is not specifically limited, but preferably is a reaction mixture or a residue obtained by distilling the solvent from the reaction mixture, wherein the reaction mixture is obtained by reacting 2-halogenoallyl isothiocyanate represented by the formula (II) with a chlorinating agent in the presence of the solvent. The reaction of the compound represented by the formula (II) with the chlorinating agent is conducted according to the methods such as JP-A No. 4-234864 and JP-A No. 2002-255948. The chlorinating agent as used herein refers chlorine and compounds releasing chlorine under the reaction conditions (such as sulfuryl chloride and phosgene). Examples of the solvent include, but not limited to, toluene, o-xylene, m-xylene, p-xylene, chlorobenzene, dichlorobenzene, dichloromethane, chloroform, 1,2-dichloroethane, carbon tetrachloride, acetonitrile and the like.

The purification from the crude product can be performed by treating the crude product with a lower alcohol and then distilling, and the treatment with the lower alcohol is preferably performed by adding the lower alcohol to the crude product, followed by stirring.

Examples of the lower alcohol used in the present invention include $C_{1-6}$ alcohols such as methanol, ethanol, propanol, isopropyl alcohol, butanol, isobutanol, sec-butanol, tert-butanol, pentanol, hexanol, among which methanol is particularly preferable.

The addition amount of the lower alcohol is usually 0.001 to 1 part by weight, preferably 0.01 to 0.1 part by weight, particularly preferably 0.01 to 0.05 part by weight to 1 part by weight of 2-halogenoallyl isothiocyanate as a starting material.

The adding time of the lower alcohol is not specifically limited as long as it is after the reaction of 2-halogenoallyl isothiocyanate as a starting material with the chlorinating agent has been completed to produce CCT, and may be before or after separation of the reaction solvent by the methods such as distillation under reduced pressure. Specifically, the lower alcohol may be added after the reaction has been completed to produce CCT, or may be added to a concentrated residue obtained by concentrating the reaction mixture after the reaction that has been completed to produce CCT, under reduced pressure to remove the reaction solvent. From the viewpoint of the industrial practice, a method in which the lower alcohol is added after recovering a reaction solvent has an excellent characteristic that the reaction solvent can be reused. After addition of the lower alcohol, a mixture is stirred.

The temperature of adding the lower alcohol and that of stirring after the addition can be varied within the relatively wide range. Generally, these adding and stirring temperatures are, usually 0° C. to 100° C., preferably 10° C. to 80° C., more preferably 20° C. to 60° C. The stirring period after the addition of the lower alcohol is usually 10 minutes to 4 hours, preferably 30 minutes to 2 hours.

Treatment with the lower alcohol may be performed under reduced or increased pressure, but is usually performed under atmospheric pressure.

Distillation after the treatment with the lower alcohol may be performed under the whole distilling conditions without refluxing after an ingredient having low boiling point is fractionated as an initial distillate, and thereby CCT can be obtained as a main distillate. The distillation is performed within the temperature range in which CCT and the distillation residue are not thermally decomposed. Specifically, the distillation is performed usually not more than 200° C., preferably not more than 124° C. of temperature inside the distiller. The distillation is also performed usually not more than 10 kPa, preferably not more than 3 kPa of pressure inside the distiller.

EXAMPLES

The present invention is further described in detail by the following Examples, but not limited by those Examples in any way.

Example 1

A mixture of 1022 kg of 2-chloroallyl isothiocyanate and 1298 kg of toluene was heated to 45° C., and was added dropwise with 1095 kg of sulfuryl chloride over 3 hours. The mixture was stirred at 45° C. for 2 hours and further stirred at 80° C. for 1 hour, and then heated under reduced pressure, and thereby 1169 kg of toluene was distilled off and recovered. The concentrated residue was cooled to 39° C., and then added with 22 kg of methanol. The mixture was stirred at 60° C. for 1 hour, and then distilled to fractionate 128 kg of initial distillate. Distillation under reduced pressure (whole distilling conditions: reflux ratio for the main distillate is 0, pressure inside the distiller: 0.7 to 1.0 kPa, top temperature: 71 to 95° C.) was further performed for 18 hours to give 956 kg of CCT in 98.3% purity (yield: 78%).

Example 2

A mixture of 1000 kg of 2-chloroallyl isothiocyanate and 1297 kg of toluene was heated to 45° C., and was added dropwise with 1071 kg of sulfuryl chloride over 3 hours. The mixture was stirred at 45° C. for 2 hours and further stirred at 80° C. for 1 hour, and then heated under reduced pressure, and thereby 1169 kg of toluene was distilled off and recovered. The concentrated residue was cooled to 38° C., and then added with 22 kg of methanol. The mixture was stirred at 60° C. for 1 hour, and then distilled to fractionate 120 kg of initial distillate. Distillation under reduced pressure (whole distilling conditions: reflux ratio for the main distillate is 0, pressure inside the distiller: 0.5 to 1.6 kPa, top temperature: 72 to 91° C.) was further performed for 18 hours to give 970 kg of CCT in 98.3% purity (yield: 81%).

Comparative Example 1

A mixture of 1066 kg of 2-chloroallyl isothiocyanate and 1297 kg of toluene was heated to 45° C., and was added dropwise with 1131 kg of sulfuryl chloride over 3 hours. The mixture was stirred at 45° C. for 2 hours and further stirred at 80° C. for 1 hour, and then heated under reduced pressure, and thereby 1170 kg of toluene was distilled off and recovered. 101 kg of initial distillate was fractionated from the concentrated residue. Distillation under reduced pressure (whole distilling conditions: reflux ratio for the main distillate is 0, pressure inside the distiller: 0.8 to 1.3 kPa, top temperature: 71 to 88° C.) was further performed for 23 hours to give 964 kg of CCT in 91.4% purity (yield: 70%).

Comparative Example 2

A mixture of 1021 kg of 2-chloroallyl isothiocyanate and 1296 kg of toluene was heated to 45° C., and was added dropwise with 1092 kg of sulfuryl chloride over 3 hours. The mixture was stirred at 45° C. for 2 hours and further stirred at 80° C. for 1 hour, and then heated under reduced pressure, and thereby 1114 kg of toluene was distilled off and recovered. 82 kg of initial distillate was fractionated from the concentrated residue. Distillation under reduced pressure (purification conditions: reflux ratio for the main distillate is (refluxing amount/distilled amount)=(25/120 for the first half) turned to (70/70 for the last half), pressure inside the distiller: 1.1 to 1.5 kPa, top temperature: 80 to 90° C.) was further conducted for 45 hours to give 911 kg of CCT in 98.0% purity (yield: 74%).

INDUSTRIAL APPLICABILITY

According to the purification process of the present invention, highly purified 2-chloro-5-chloromethyl-1,3-thiazole can be obtained in high yield with a simple equipment under good operable conditions in a short time. Therefore, the purification process of the present invention is extremely useful industrially.

The invention claimed is:

1. A process for purifying 2-chloro-5-chloromethyl-1,3-thiazole represented by the formula (I):

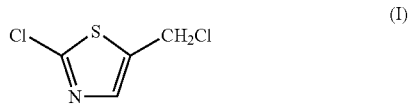

which comprises:
treating a crude 2-chloro-5-chloromethyl-1,3-thiazole represented by the formula (I) with a lower alcohol, and then
distilling the treated 2-chloro-5-chloromethyl-1,3-thiazole at not more than 200° C. and not more than 10 kPa.

2. The process for purifying 2-chloro-5-chloromethyl-1,3-thiazole according to claim 1, wherein the crude 2-chloro-5-chloromethyl-1,3-thiazole is treated with the lower alcohol by adding the lower alcohol to the crude 2-chloro-5-chloromethyl-1,3-thiazole, followed by stirring.

3. The process for purifying 2-chloro-5-chloromethyl-1,3-thiazole according to claim 2, wherein the lower alcohol is methanol.

4. The process for purifying 2-chloro-5-chloromethyl-1,3-thiazole according to claim 1, wherein the crude 2-chloro-5-chloromethyl-1,3-thiazole is a reaction mixture obtained by reacting a 2-halogenoallyl isothiocyanate represented by the general formula (II):

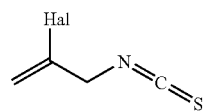

wherein Hal represents a chlorine atom or a bromine atom, with a chlorinating agent in the presence of a solvent, or
wherein the crude 2-chloro-5-chloromethyl-1,3-thiazole is a residue obtained by distilling the solvent from the reaction mixture.

5. The process for purifying 2-chloro-5-chloromethyl-1,3-thiazole according to claim 4, wherein the lower alcohol is methanol.

6. The process for purifying 2-chloro-5-chloromethyl-1,3-thiazole according to claim 5, wherein Hal is a chlorine atom.

7. The process for purifying 2-chloro-5-chloromethyl-1,3-thiazole according to claim 4, wherein Hal is a chlorine atom.

8. The process for purifying 2-chloro-5-chloromethyl-1,3-thiazole according to claim 4, wherein the crude 2-chloro-5-chloromethyl-1,3-thiazole is a residue obtained by distilling the solvent from the reaction mixture.

9. The process for purifying 2-chloro-5-chloromethyl-1,3-thiazole according to claim 8, wherein the lower alcohol is methanol.

10. The process for purifying 2-chloro-5-chloromethyl-1,3-thiazole according to claim 9, wherein Hal is a chlorine atom.

11. The process for purifying 2-chloro-5-chloromethyl-1,3-thiazole according to claim 8, wherein Hal is a chlorine atom.

12. The process for purifying 2-chloro-5-chloromethyl-1,3-thiazole according to claim 1, wherein the lower alcohol is methanol.

* * * * *

UNITED STATES PATENT AND TRADEMARK OFFICE
CERTIFICATE OF CORRECTION

PATENT NO. : 7,846,304 B2
APPLICATION NO. : 12/385038
DATED : December 7, 2010
INVENTOR(S) : Oga et al.

It is certified that error appears in the above-identified patent and that said Letters Patent is hereby corrected as shown below:

On the Front Page

In Item (73) Assignee, after "Toyo Boseki Kabushiki Kaisha, Osaka (JP)" please add ": Sumitomo Chemical Company, Limited, Tokyo (JP)"

Signed and Sealed this
Ninth Day of August, 2011

David J. Kappos
*Director of the United States Patent and Trademark Office*

UNITED STATES PATENT AND TRADEMARK OFFICE
CERTIFICATE OF CORRECTION

PATENT NO.         : 7,846,304 B2
APPLICATION NO.    : 12/385038
DATED              : December 7, 2010
INVENTOR(S)        : Oga et al.

It is certified that error appears in the above-identified patent and that said Letters Patent is hereby corrected as shown below:

On the Front Page

Item (73) Assignee, should read --Toyo Boseki Kabushiki Kaisha, Osaka (JP);

Sumitomo Chemical Company, Limited, Tokyo (JP)--

This certificate supersedes the Certificate of Correction issued August 9, 2011.

Signed and Sealed this
Eighth Day of November, 2011

David J. Kappos
*Director of the United States Patent and Trademark Office*